United States Patent [19]

Motika et al.

[11] Patent Number: 5,026,676

[45] Date of Patent: Jun. 25, 1991

[54] CATALYST FOR THE COPOLYMERIZATION OF EPOXIDES WITH $CO_2$

[75] Inventors: Stephen A. Motika, Kutztown; Timothy L. Pickering, Emmaus; Andrzej Rokicki, Alburtis; Beatrice K. Stein, Fogelsville, all of Pa.

[73] Assignees: Air Products and Chemicals, Inc., Allentown; Arco Chemical Company, Newtown Square, both of Pa.; Mitsui Petrochemical Industries Ltd., Tokyo, Japan

[21] Appl. No.: 513,325

[22] Filed: Apr. 20, 1990

Related U.S. Application Data

[63] Continuation of Ser. No. 362,894, Jun. 7, 1989, abandoned.

[51] Int. Cl.$^5$ ............................................. B01J 31/04
[52] U.S. Cl. ................................. 502/170; 528/405
[58] Field of Search .......................................... 502/170

[56] References Cited

U.S. PATENT DOCUMENTS

| | | | |
|---|---|---|---|
| 2,932,663 | 4/1960 | Kalenda et al. | 502/170 X |
| 3,248,415 | 4/1966 | Stevens | 260/463 |
| 3,506,598 | 4/1970 | Groff et al. | 502/170 X |
| 3,585,168 | 6/1971 | Inoue et al. | 260/77.5 D |
| 3,900,424 | 8/1975 | Inoue et al. | 252/428 |
| 3,953,383 | 4/1976 | Inoue et al. | 260/2 BP |
| 4,268,684 | 5/1981 | Gurgiolo | 502/170 X |
| 4,783,445 | 11/1988 | Sun | 502/170 |

OTHER PUBLICATIONS

S. Inoue et al., "Copolymerization of Carbon Dioxide and Epoxide", pp. 287–292, J. Poly. Sc. Letters 7 (1969).
K. Soga, "Altimating Copolymerization of $CO_2$ and Propylene Oxide with the Catalysts Prepared from $Zn(011)_2$ and Various Dicarboxylic Acids", Polymer Journal, vol. 13, No. 4, p. 407 (1981).
K. Soga, "Preparation of Catalysts for Use in Alternating Copolymerization Reactions of Propylene Oxide and Carbon Dioxide", Nippon Kagakkaishi, 2, 295 (1982).
K. Soga et al., "Copolymerization of Carbon Dioxide and Propylene Oxide with New Catalysts", Makromol Chem., 178, 893–897 (1977).

*Primary Examiner*—Patrick P. Garvin
*Attorney, Agent, or Firm*—William F. Marsh; James C. Simmons

[57] ABSTRACT

Zinc carboxylate catalysts for the copolymerization of carbon dioxide and epoxides are prepared by the reaction of zinc oxide with glutaric or adipic acid in an aprotic reaction solvent. Azeotropic distillation may be used to separate the water-solvent phase from the reaction mixture, or the catalyst may be separated from the reaction mixture by filtration and drying, generally without the need for repeated washings to remove active hydrogen atom sources. Examples of aprotic reaction solvents are toluene, dibutyl ether, anisole and ethyl benzoate.

11 Claims, 2 Drawing Sheets

CONTAMINATED CATALYST

CATALYST FOR THE COPOLYMERIZATION OF EPOXIDES WITH $CO_2$

This is a continuation of application Ser. No. 07/362,894, filed Jun. 7, 1989, now abandoned.

TECHNICAL FIELD OF THE INVENTION

The invention described in this Application relates to an improved catalyst and method for making said catalyst for use in the synthesis of poly(alkylene carbonate) polymers formed by the copolymerization of carbon dioxide and epoxides.

BACKGROUND OF THE INVENTION

The copolymerization of carbon dioxide with epoxides to form poly(alkylene carbonate) polymers was discovered by Inoue and co-workers (*Polymer Letters* 7, 287(1969)) and described in U.S. Pat. No. 3,585,168. Other processes are described in U.S. Pat. Nos. 3,900,424, 3,953,383 and 3,248,415. Despite the obvious economic advantage associated with the use of an abundant, low cost material like carbon dioxide, the introduction of commercial products that utilize this chemistry has been very slow. One reason has been the practical difficulty in handling the organometallic catalysts required on a commercial scale.

The Inoue catalyst system was prepared by the reaction of diethylzinc with materials containing active hydrogen compounds., e.g., water, dicarboxylic acids, or dihydric phenols. Typical catalyst productivities ranged from 2.0 to 10.0 grams of polymer per gram of catalyst used, with more results falling at the low end of the range. Long polymerization times—24 to 48 hours—were required in order to achieve satisfactory yields and product molecular weight. Some of the phenol-containing catalysts form highly colored material on exposure to air. This can lead to discolored products because of the difficulty in removing all traces of color bodies from the polymer. A high ratio of catalyst to polymer was required to achieve satisfactory yields; therefore, separation of the catalyst from the polymer at the conclusion of polymerization was difficult. The Inoue catalysts also generated noticeable amounts of cyclic carbonate by-products and polyether homopolymer that had to be removed from the desired polycarbonate polymer.

Diethylzinc is a highly reactive, pyrophoric material. Stringent handling requirements are necessary to prevent the risk of fire when the material is to be used on a commercial scale. When the polymerization reaction is finished, extensive purification procedures are necessary to remove all traces of catalyst from the polymer. Because of its general lack of stability, sensitivity to moisture and to other catalyst poisons, the active catalyst material is prepared from diethylzinc immediately prior to polymerization. This is a distinct disadvantage since catalyst quality cannot be determined prior to polymerization. These considerations, along with the generally low catalyst productivity, have stimulated the search for improved catalyst materials for epoxide/-$CO_2$ polymerizations.

Zinc carboxylates have also been described as effective catalysts for $CO_2$ polymerization. Since these are stable materials with none of the handling problems associated with diethylzinc, they represent interesting candidates for a practical commercial catalyst system.

Soga and co-workers reported that reaction products of zinc hydroxide and aliphatic dicarboxylic acids exhibited high activity for the copolymerization of carbon dioxide and propylene oxide (*Polymer J.* 13(4), 407(1981)). A variety of acids were tested, but only adipic and glutaric acid produced catalysts with higher activity than the known diethylzinc catalysts. Catalysts prepared from aromatic dicarboxylic acids were essentially inert under the Soga polymerization conditions.

Soga reported another approach to improve catalyst activity that involved supporting the catalyst on an inert OXide Carrier (*Nippon Kagakkaishi* 2, 295(1982)). Using a support increased the surface area of active catalyst material and was expected to lead to more efficient production of polymer. However, the supported catalysts were no more effective than the standard diethylzinc based catalysts.

The metal salts of acetic acid are a third type of catalyst material known to bring about copolymerization of $CO_2$ with epoxides (Soga. et al., *Makromol. Chem.* 178, 893(1977)). Only zinc and cobalt produced alternating copolymers from $CO_2$ and epoxides, and the activity of these catalysts was lower than that observed with diethylzinc derived catalysts.

The synthetic methods described by Inoue, particularly the handling of the organometallic catalyst and its removal from the polymer, proved to be impractical for the production of sufficient polymer for industrial testing and evaluation., therefore, an improved method of polymer preparation was sought. Of all the catalyst systems reported in the literature up to that time, only zinc carboxylates based on adipic or glutaric acid appeared to have the potential for practical use on a commercial scale.

Soga et al reported a synthetic procedure for production of a zinc carboxylate catalyst involving reaction of zinc hydroxide with glutaric acid in alcoholic solvents. The catalysts so obtained experimentally were inconsistent in their polymerization behavior. Some preparations gave products with good productivity while other, seemingly identical, preparations were inactive or had low productivity. In the course of investigating the causes of the inconsistent behavior, an improved method of catalyst preparation was developed. A description of the improved method and the preferred embodiments is described in the next section.

It has also been reported that soluble zinc catalysts can be prepared by the reaction of zinc oxide or zinc salts with a dicarboxylic acid anhydride or monoester in a suitable solvent such as the lower alcohols, ketones, esters and ethers as disclosed by Sun in U.S. Pat. No. 4,783,445.

In the prior art methods, preparation of the catalysts involved repeated washing and purification steps to produce an active catalyst.

BRIEF SUMMARY OF THE INVENTION

This invention provides an improved procedure for the preparation of zinc carboxylate catalysts used in the preparation of copolymers of epoxide materials and carbon dioxide. Specifically, substantially improved zinc carboxylate catalysts for the copolymerization of epoxides and carbon dioxides are produced by reacting zinc oxide with a dicarboxylic acid. preferably glutaric or adipic acids, in a reaction medium comprising an aprotic solvent, preferably a solvent that forms an azeotrope with or is immiscible with water. The solid catalyst may then be separated from the reaction mixture and dried. Alternatively, the water of reaction may be removed by azeotropic distillation with the reaction solvent, and the resulting catalyst slurry may be used directly. The method used to prepare the zinc carboxylate has a dramatic effect on its performance as a catalyst, even though the empirical composition and the spectral properties of the carboxylates prepared by different methods are virtually identical. The present method produces a catalyst substantially free of residual water or other active hydrogen sources which are deleterious to its activity in the copolymerization of carbon dioxide and epoxides, but without the necessity of expensive and time-consuming repeated washing and purification steps.

DETAILED DESCRIPTION OF THE INVENTION

Figure 1:
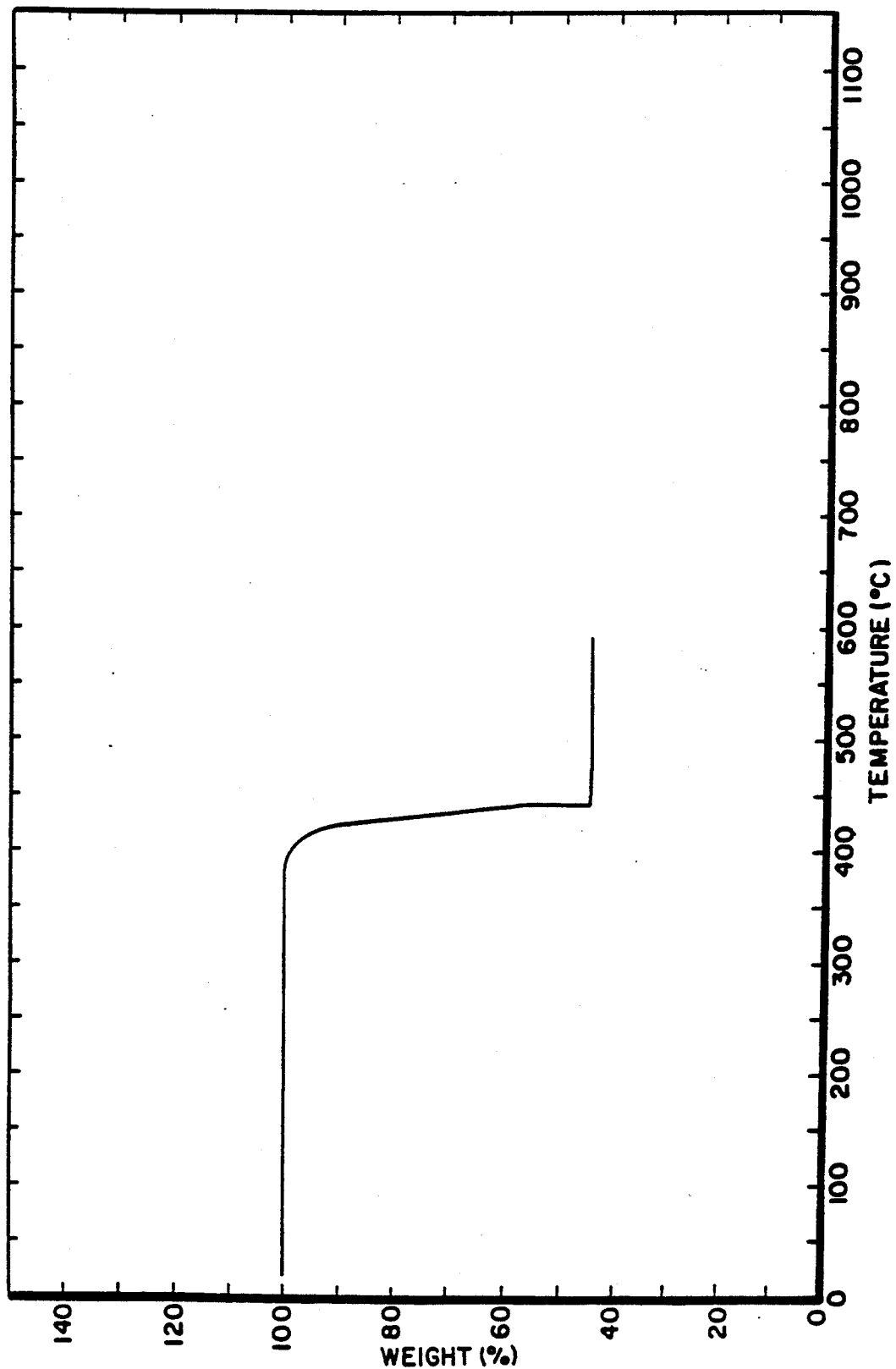
FIGS. 1 and 2 show the effect of temperature on the catalyst.

The zinc carboxylate catalysts of this invention are made by reacting reagent grade zinc oxide, in a slight molar excess, with a dicarboxylc acid, preferably either glutaric or adipic acid, in the presence of an aprotic solvent, that is, a solvent without active hydrogen atoms. A suitable test for active hydrogen atoms is the Zerewitinoff determination Os described in standard organic chemistry texts. Preferably, the solvent forms an azeotrope with or is immiscible with water formed by the reaction of the zinc oxide and dicarboxylic acid to facilitate the separation of the water produced by the zinc oxide/acid reaction from the insoluble catalyst. The reaction can be carried out from about room temperature (20° C.) to about 85° C. and preferably up to about 55° C. The reaction, depending on dicarboxylic acid used, takes about one to about four hours at 55° C. The fine zinc carboxylate catalyst powder formed under the reaction conditions can be substantially separated from the water in the reaction medium by azeotropic distillation of the solvent/water mixture or separated by filtration from the liquid phase and then dried.

The product is a fine, white powder zinc carboxylate ready for use in the copolymerization of epoxides and carbon dioxide as generally taught in prior art processes utilizing other catalysts including, but not limited to, those processes described in U.S. Pat. Nos. 3,585,168 and 3,953,383.

A more detailed description of the invention and its methods of practice are described in the following examples.

EXAMPLE 1

Prior Art Catalyst Preparation Method

To a 300 ml glass reactor containing 150 ml of solvent were added 50 mmol of a dicarboxylic acid and 50 mmol of $Zn(OH)_2$. The mixture was allowed to stir for four hours at 55° C. The solid product was filtered off, washed repeatedly with the solvent and dried in vacuo at room temperature.

EXAMPLE 2

Catalyst Preparation Method A

To a one liter, three neck, round bottom flask equipped with stirrer, condenser, Dean-Stark trap and heating bath was added 0.50 moles zinc oxide (Fisher reagent grade) and 350 ml reaction solvent. To this was added 0.45 moles of dicarboxylic acid dissolved or slurried in the reaction solvent. The mixture was heated for 4 hours at 55° C. with vigorous stirring. On cooling, the solids were filtered off and dried overnight in a vacuum oven at 80° C.

EXAMPLE 3

Catalyst Preparation Method B

To a one liter, three neck, round bottom flask equipped with stirrer, condenser, Dean-Stark trap and heating bath was added 0.50 moles zinc oxide (Fisher reagent grade) and 350 ml reaction solvent. To this was added 0.45 moles of dicarboxylic acid dissolved or slurried in the reaction solvent. The mixture was heated for 2 hours at 55° C. with vigorous stirring. The mixture was then brought to reflux and held there until azeotropic removal of water ceased. On cooling, the solids were filtered off and dried overnight in a vacuum oven at 80° C.

EXAMPLE 4

Effect of Dicarboxylic Acid Reactant

To a one liter, three neck, round bottom flask equipped with stirrer, condenser and heating bath was added 50.0 gm (0.61 moles) zinc oxide (Fisher reagent grade) and 350 ml reagent grade ethanol. To this was added a solution of 76.0 gm (0.57 moles) of dicarboxylic acid dissolved in 400 ml of ethanol. The slurry was heated for 4 hours at 55° C. with vigorous stirring. On cooling, the solids were filtered off and dried overnight in a vacuum oven at 80° C. The yield was quantitative. In a similar fashion, the catalysts described in Table II were prepared and screened using the polymerization method described above.

EXAMPLE 5

Catalyst Productivity Screening Method

Three to five grams of zinc carboxylate catalyst prepared according to the procedure described in Method A or B was placed in the bottom section of a 300 ml capacity Parr stirred autoclave reactor. The reactor body and catalyst were heated in a nitrogen purged oven at 125° C. for 8-10 hours, then cooled to room temperature while maintaining the nitrogen atmosphere. The autoclave body was transferred to a gloved dry box where 150 gm of methylene chloride and 50 gm of propylene oxide were added. Both materials were reagent grade chemicals, and had been dried and stored over 4A molecular sieves. The autoclave head was attached to the body and the entire assembly was transferred to a pressure cell. The reactor was connected to nitrogen and $CO_2$ sources via a three-way valve. The autoclave was pressurized to 300 psi with $N_2$, slowly vented to atmospheric pressure and repressurized to 250 psi with $CO_2$. The reactor was then heated to an internal temperature of 85° C. The $CO_2$ pressure increased to 450 psi and was maintained at this level throughout the course of the polymerization via a constant pressure feed valve. After 4 hours, the reactor was cooled to room temperature, the pressure was released and the contents of the reactor were emptied into a crystallizing dish. The solvent and unreacted propylene oxide were allowed to evaporate under ambient conditions for 12 hours, then the residue was dried under vacuum at room temperature for an additional 12 hours. The white, leathery polymeric material obtained was weighed to determine gross yield. After correcting the gross weight for the amount of catalyst charged, the catalyst efficiency was reported as grams of polymer produced per gram of catalyst used.

Further analysis of the crude and purified product by FTIR and NMR analysis showed the polymer to have substantially a 1:1 alternating structure as reported by Inoue and others. The zinc carboxylate catalysts studied in this work produced negligible amounts of methanol soluble polyether polymer. According to literature reports, the latter materials were usually present as by-products when diethylzinc based catalysts were used. The crude product was shown to contain 3-5% of cyclic propylene carbonate by-product by FTIR. The amount of cyclic by-product formed was relatively constant in all runs using zinc carboxylate catalysts.

EXAMPLE 6

Effect of Catalyst Synthesis Reaction Temperature

To a one liter, three neck, round bottom flask equipped with stirrer, condenser, Dean-Stark trap and heating bath was added 50.0 gm (0.61 moles) zinc oxide (Fisher reagent grade) and 350 ml toluene. To this was added a slurry of 76.0 gm (0.57 moles) of glutaric acid in 400 ml of toluene. The slurry was heated for 4 hours at the temperature indicated with vigorous stirring. The mixture was then brought to reflux and held there until removal of water ceased. The mixture was cooled and the white solid was filtered off and dried overnight at 80° C. The yield was quantitative.

The above examples and the data shown in the tables demonstrate that the zinc source used for synthesis proved to have an important effect on catalyst performance as shown in Table I. The prior art method used $Zn(OH)_2$ as the zinc source. While freshly prepared zinc hydroxide worked reasonably well, purchased zinc hydroxide proved unacceptable because of low reactivity. ZnO was found to be an effective zinc source and a more practical alternative since purchased material had equivalent reactivity to laboratory prepared material. Zinc sources with more ionic character, such as zinc acetate and zinc carbonate, produce catalysts with lower activity than those prepared from zinc oxide, even when the same dicarboxylic acid is used.

TABLE I
EFFECT OF ZINC SOURCE
ON CATALYST PERFORMANCE*

| Zinc Source | Catalyst Prep. Method | Reaction Solvent | Catalyst** Productivity |
|---|---|---|---|
| $Zn(OH)_2$ | B | Toluene | 0 |
| $Zn(OH)_2$ | A | Methanol | 4 |
| $Zn(CO_3)_2$ | B | Toluene | 2 |
| $Zn(CO_3)_2$ | A | Methanol | 1 |
| $Zn(OAc)_2$ | B | Toluene | 0 |
| $Zn(OAc)_2$ | A | Methanol | 2 |
| ZnO | B | Toluene | 22 |
| ZnO | A | Toluene | 17 |
| ZnO | A | Methanol | 8 |

*Dicarboxylic acid in each case was glutaric acid.
**Grams of product obtained per gram of catalyst used As shown by Table II, the most preferred dicarboxylic acids for catalyst preparation are either glutaric acid or adipic acid.

TABLE II
EFFECT OF ACID GROUP
ON CATALYST PERFORMANCE

| Acid Used | Catalyst Prep. Method | Reaction Solvent | Catalyst** Productivity |
|---|---|---|---|
| Oxalic | A | Ethanol | 0.1 |
| Malonic | A | Ethanol | 0.0 |
| Succinic | A | Water | 0.0 |
| Glutaric | A | Ethanol | 7.0 |
| Adipic | A | Ethanol | 7.0 |
| Maleic | A | Ethanol | 0.7 |

**Grams of product obtained per gram of catalyst used

The ratio of dicarboxylic acid to zinc salt used plays a role in catalyst performance, and is important from an operational perspective. As reported in the case of catalysts prepared from diethylzinc/water, the highest activity is observed when the reactant mole ratio is 1.0. However the presence of small amounts of free acid is deleterious to catalyst performance. Although excess acid can be removed by thorough washing, this entails extra steps in the procedure. We have found the washing steps can be avoided by using a stoichiometric excess of zinc oxide in the synthesis. Since zinc oxide is inert in the polymerization process, it need not be separated from the catalyst. A large excess of zinc oxide is undesirable because it dilutes the amount of active catalyst present per pound of catalyst/oxide mixture. On the other hand, a sufficient excess should be used to insure complete conversion of the acid. From practical considerations, we have found a 2-5 mole percent excess of zinc oxide to be most preferable. An excess of the dicarboxylic acid is to be avoided.

The influence of solvent used for catalyst preparation on performance is shown in Table III. Unexpectedly superior catalyst performance is obtained when solvents that are aprotic are used as the catalyst synthesis medium. Preferred are solvents that form azeotropes with water, and contain oxygen heteroatoms. Catalyst performance is slightly lower, but still acceptable, when aprotic hydrocarbon solvents are used. Solvents that are miscible with water but contain no active hydrogen atoms (e.g., dioxane, acetone) give catalysts of intermediate activity. Water and lower alcohols that are miscible with water or that have active hydrogen atoms give catalysts of lowest activity.

TABLE III
EFFECT OF PREPARATION SOLVENT
ON CATALYST PERFORMANCE

| Reaction Solvent | Catalyst Prep. Method | Acid Used | Catalyst** Productivity | $Mn \times 10^{-3}$ |
|---|---|---|---|---|
| Water | A | Glutaric | 3 | — |
| Methanol | A | Glutaric | 8 | 36 |
| Ethanol | A | Glutaric | 7 | 80 |
| i-Propanol | A | Glutaric | 2 | — |
| 70% i-PrOH | A | Glutaric | 5 | 55 |
| Tetrahydrofuran | A | Glutaric | 6 | 40 |
| Dioxane | A | Glutaric | 8 | 25 |
| Acetone | A | Glutaric | 5 | 42 |
| Hexane | B | Glutaric | 9 | 77 |
| Toluene | B | Glutaric | 22 | 79 |
| Toluene | A | Glutaric | 17 | 111 |
| Toluene | B | Adipic | 19 | 99 |
| Methanol | A | Adipic | 0 | — |
| Dibutyl Ether | B | Glutaric | 26 | 116 |
| Dibutyl Ether | A | Glutaric | 21 | 98 |
| Anisole | B | Glutaric | 22 | 173 |
| Ethyl Benzoate | B | Glutaric | 23 | 111 |

**Grams of product obtained per gram of catalyst used

Another item affecting catalyst performance is the reaction temperature and temperature profile used for the synthesis reaction, as shown in Table IV, for reactions run under the conditions of Example 6. The most preferred range for the initial reaction temperature is from room temperature to about 55° C. If higher initial temperatures are used, for example, by heating immediately to the azeotrope temperature when high boiling azeotropic solvents are used, catalyst performance is adversely affected. On the other hand, reactions carried out below room temperature do not improve catalyst performance, but require longer times for complete conversion of reactants.

TABLE IV

EFFECT OF REACTION TEMPERATURE ON CATALYST PERFORMANCE

| Reaction Temperature | Catalyst* Productivity | $Mn \times 10^{-3}$ |
|---|---|---|
| 25 | 16 | 126 |
| 30 | 17 | 161 |
| 40 | 16 | 118 |
| 55 | 13 | 167 |
| 85 | 10 | 130 |

**Grams of product obtained per gram of catalyst used.

Figure 2:
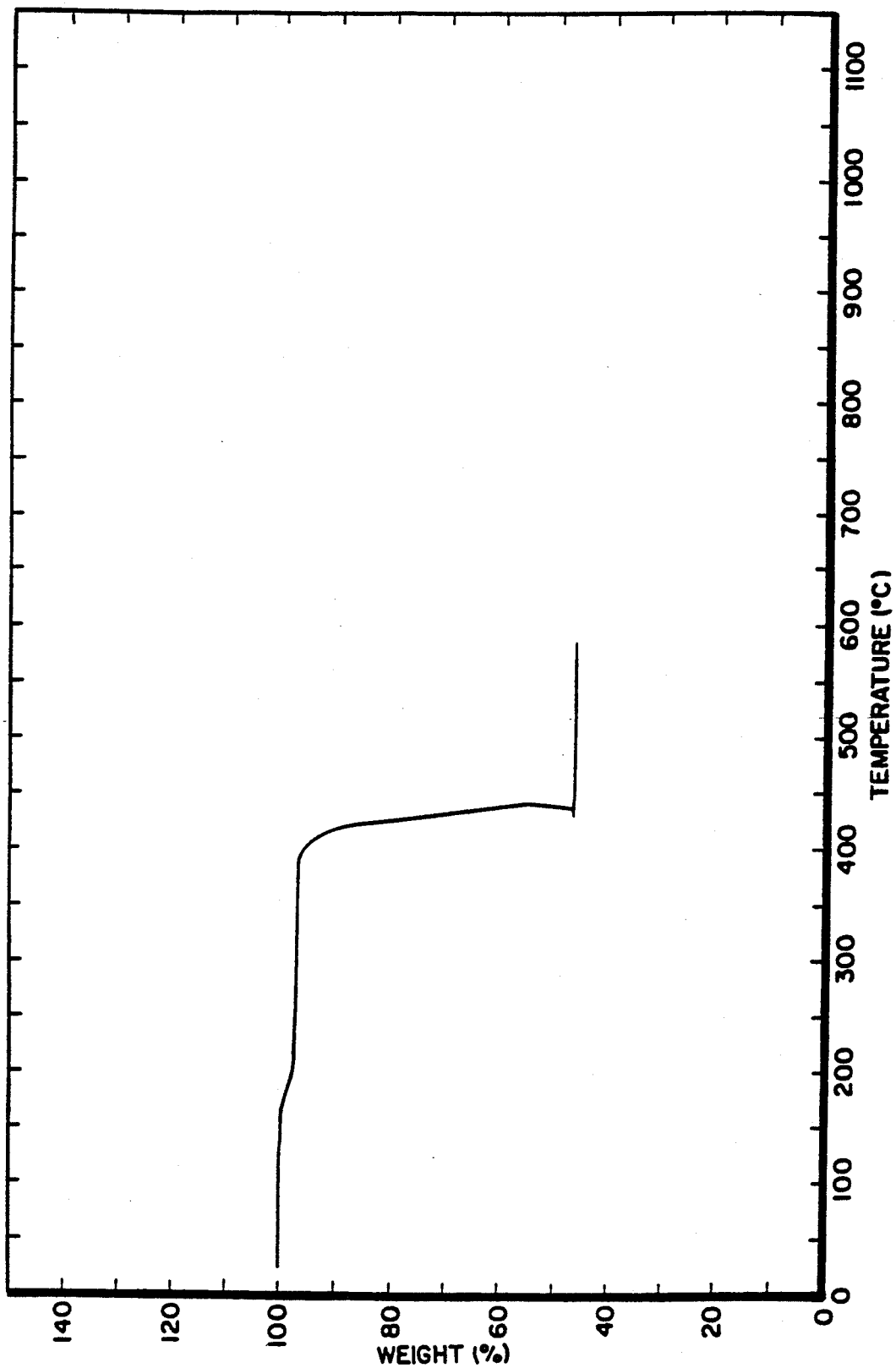

The reaction is complete in one to three hours at 50° C. when glutaric acid is used as the acid source. Adipic acid requires longer reaction time and is more difficult to drive to complete conversion. The extent of conversion is conveniently monitored by thermogravimetric analysis. Pure zinc carboxylates decompose at around 425° to 450° C. to form zinc oxide. There is no detectable weight loss below 400° C. as shown in FIG. 1. If traces of unreacted acid or solvent remain in the product, their presence will be indicated by weight loss occurring below 400° C. as shown in FIG. 2.

We claim:

1. A zinc carboxylate catalyst for the copolymerization of carbon dioxide and epoxides to form poly (alkylene carbonates) prepared by reacting zinc oxide with a dicarboxylic acid selected from the group consisting of glutaric acid and adipic acid in an aprotic reaction solvent.

2. The catalyst of claim 1 wherein the aprotic reaction solvent is selected from the group consisting of toluene, dibutyl ether, anisole and ethyl benzoate.

3. The catalyst of claim 1 wherein the reaction solvent forms an azeotrope with water.

4. The catalyst of claim 1 wherein the reaction solvent is immiscible with water.

5. The catalyst of claim 1 wherein the zinc oxide is present in the reaction mixture in stoichiometric excess.

6. The catalyst of claim 5 wherein the zinc oxide is present in the reaction mixture in stoichiometric excess of from about 2 to about 5 mole percent excess.

7. A process for the preparation of a zinc carboxylate catalyst for the copolymerization of carbon dioxide and epoxides to form poly (alkylene carbonates) comprising reacting zinc oxide with a dicarboxylic acid selected from the group consisting of glutaric acid and adipic acid in an aprotic reaction solvent.

8. The process of claim 7 wherein the reaction is carried out at a temperature of from about 20° C. to about 55° C.

9. The process of claim 8 wherein the reaction solvent is selected from the group consisting of toluene, dibutyl ether, anisole and ethyl benzoate.

10. A process for the preparation of a zinc carboxylate catalyst for the copolymerization of carbon dioxide and epoxides to form poly (alkylene carbonates) comprising reacting a stoichiometric excess of zinc oxide with a dicarboxylic acid selected from the group consisting of glutaric acid and adipic acid in a reaction solvent selected from the group consisting of toluene, dibutyl ether, anisole and ethyl benzoate, separating the zinc carboxylate from the reaction solvent, and drying the zinc carboxylate catalyst.

11. The process of claim 7 wherein the water of reaction is separated from the catalyst by azeotropic distillation with the reaction solvent.

* * * * *